US00PP26954P3

(12) United States Plant Patent
Acosta

(10) Patent No.: US PP26,954 P3
(45) Date of Patent: Jul. 19, 2016

(54) AVOCADO TREE NAMED 'LALI'

(50) Latin Name: *Persea americana*
Varietal Denomination: Lali

(71) Applicant: Acosta Farms, Inc., Miami, FL (US)

(72) Inventor: Alcides Acosta, Coral Gables, FL (US)

( * ) Notice: Subject to any disclaimer, the term of this patent is extended or adjusted under 35 U.S.C. 154(b) by 37 days.

(21) Appl. No.: 13/999,231

(22) Filed: Jan. 31, 2014

(65) Prior Publication Data

US 2015/0223379 P1 Aug. 6, 2015

(51) Int. Cl.
*A01H 5/00* (2006.01)

(52) U.S. Cl.
USPC ..... Plt./200

(58) Field of Classification Search
USPC ..... Plt./200
See application file for complete search history.

(56) References Cited

U.S. PATENT DOCUMENTS

PP23,885 P3 * 9/2013 Pflum ..... Plt./200

* cited by examiner

*Primary Examiner* — Susan McCormick Ewoldt
(74) *Attorney, Agent, or Firm* — Michael C. Cesarano, P.A.

(57) ABSTRACT

The 'Lali' avocado is of medium size, average 14-18 ounces and being about 3.5 inches in diameter and 5 inches in length. The fruit matures and can be picked in late February and March. The fruit is an ovate berry having a seed that is tight in the cavity and is 2 to 2.5 inches long and dark brown in color.

3 Drawing Sheets

Latin name: *Persea americana.*
Varietal denomination: 'Lali'.

BRIEF SUMMARY OF THE INVENTION

The tree arose as a root stock sprout from an avocado tree in a cultivated 85 acre avocado grove located at in Miami-Dade County, Fla., at 355014 Southwest 209$^{th}$ Avenue, Miami, Fla. 33034. The tree is estimated to be approximately 15 years old and has been in production for at least 10 years. Its origin is unknown. Its fruit can be stored at temperatures above 50° Fahrenheit.

Parentage is unknown as the tree was discovered, and is of a wild nature.

An analysis of the microsatellite pattern from this avocado against 15 known varieties ('Lula' (not patented), 'Simmonds' (not patented), 'Monroe' (U.S. Plant Pat. No. 261), 'Choquette' (not patented), 'Semil-34' (not patented), 'Semil-43' (not patented), 'Melendez' (not patented), 'Hall' (not patented), 'Booth' (not patented), 'Hardee' (not patented), 'April' (not patented), 'Carla' (U.S. Plant Pat. No. 16,594), 'Pollock' (not patented), 'Bernecker' (not patented) and 'Donnie' (not patented)) revealed no matches.

Asexual propagation was attained in 2010 in Miami-Dade County, Fla. when the plant was approximately 12 years old. Asexual reproduction was achieved by grafting cuttings of the tree onto new avocado seedlings. The fruit is ripened and is sufficient for harvesting in late February to late March. Lali presents resistance to *cercospora purpurea* pathogens.

Measurements are from the year, 2015. Botanical descriptions are described using "Exotica Pictorial Cyclopedia of Exotic Plants," A.B. Graf, page 1834, "Botanical Terms Illustrated." Color is described using the HEX value designation obtained from the web site, cloford.

DETAILED BOTANICAL DESCRIPTION

Figure 1:
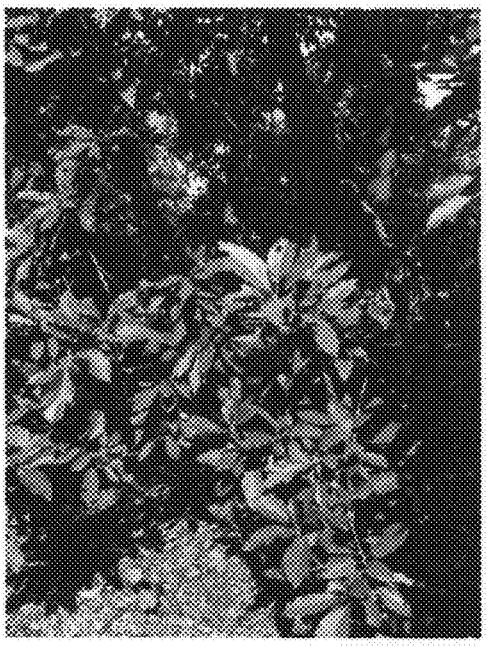
FIG. 1 shows the leaves and branches at a lower portion of the 'Lali' avocado tree.
Figure 4:
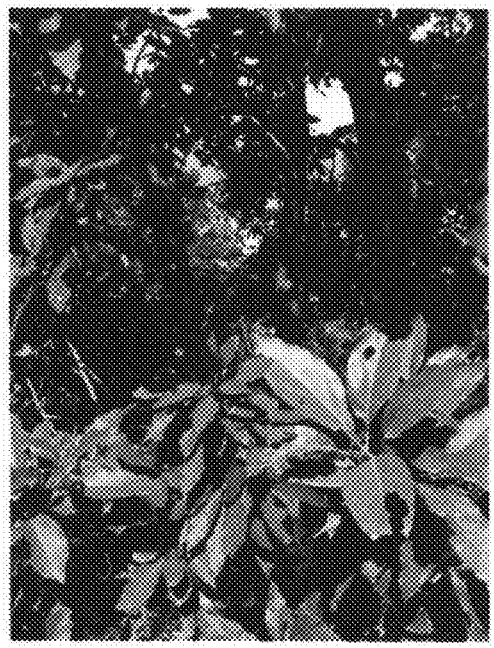
FIG. 4 shows a closer view of the leaves of FIG. 3.
Figure 6:
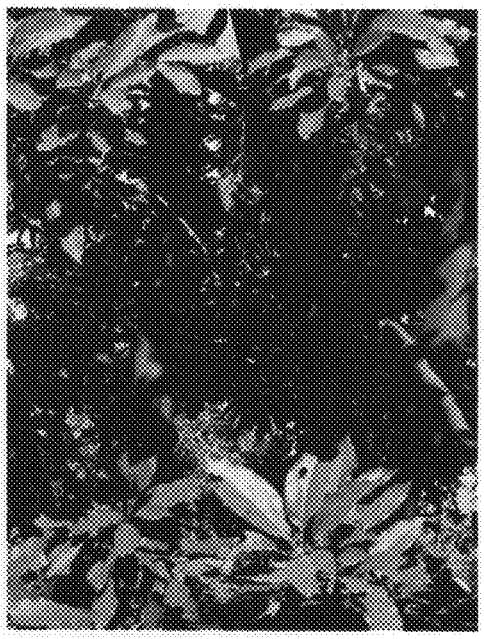
FIG. 6 shows the density of leaves and branches of the 'Lali' avocado tree.
Figure 7:
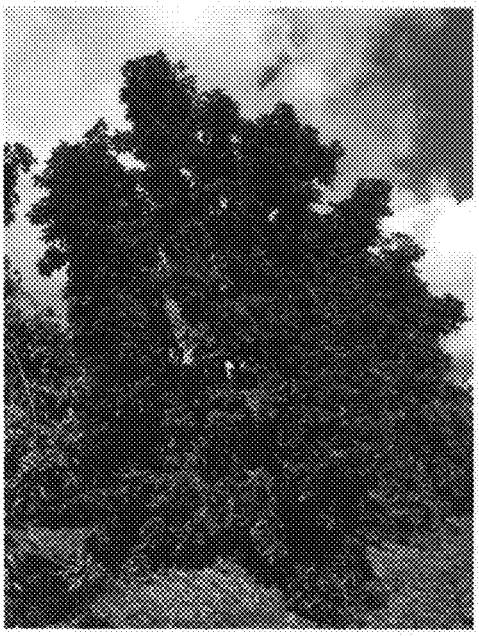
FIG. 7 shows a view of an entire 'Lali' avocado tree.
Figure 9:
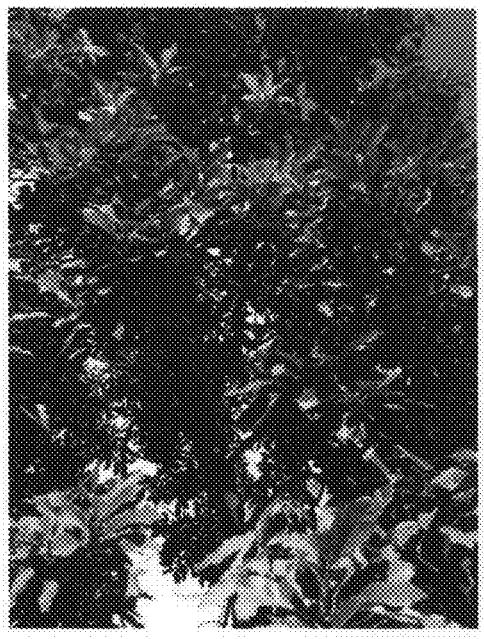
FIG. 9 shows a view of the top level of the 'Lali' avocado tree.

The tree presents a vigorous weeping upright growth habit with a spread of 18' and 25' high (limited by common pruning practices for avocado groves in South Florida), as shown in FIG. 7. As shown in FIGS. 1, 4 and 6, the diameter of the main trunk is 23"-25". The main trunk splits into 4 sub trunks or branches, each about 3-4 inches in width with the vertical sub trunk splitting into smaller branches, FIG. 9. Younger branches are light to medium green (HEX value#CAC673, khaki 3) with a smooth surface with raised lenticels. Older branches are of a brown/bisque coloration (HEX value #8B7D6B, bisque 4) having a woody surface with lenticels striated. Green wood is of a green color (HEX value #669966). The trunk is corky and smooth to slightly rough with lenticels prominently striated. Lenticels are prominent on limbs of green wood but merge in a striated pattern as bark ages and becomes corkier. The bark of the trunk is an indeterminate brown to greenish brown (HEX value #8B864B, khaki 4) owing to a repeated copper hydroxide spray regimen. New shoots are light green in color (HEX value #90EE90) and the foliage is dark green (HEX value #8FBC8F) at maturity and burgundy (HEX value #8B4C39) at a young stage. The main trunk at 2 feet in height has a circumference of 36" and a diameter of approximately 11.5". One main scaffold limb arises from the main trunk and is 24" in circumference at a height of 4 feet and is approximately 7.5" in diameter. Limbs range from 3'-10' from the main axis of the tree, and taper from 3.5" at tree axis to 0.75" at the most distal end.

Figure 2:
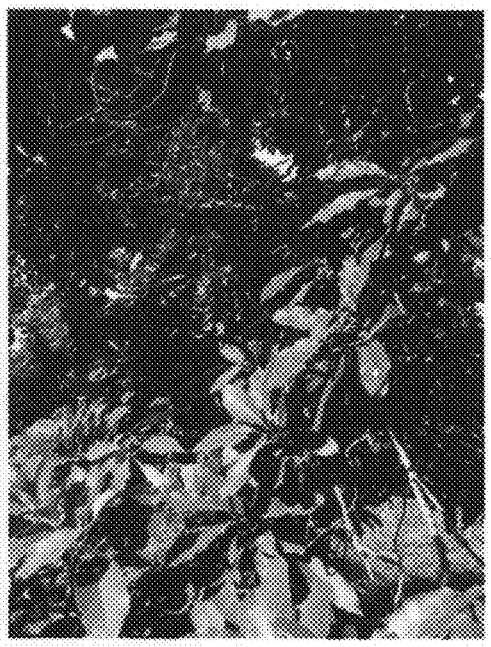
FIG. 2 shows a closer view of the leaves and branches in FIG. 1.
Figure 3:
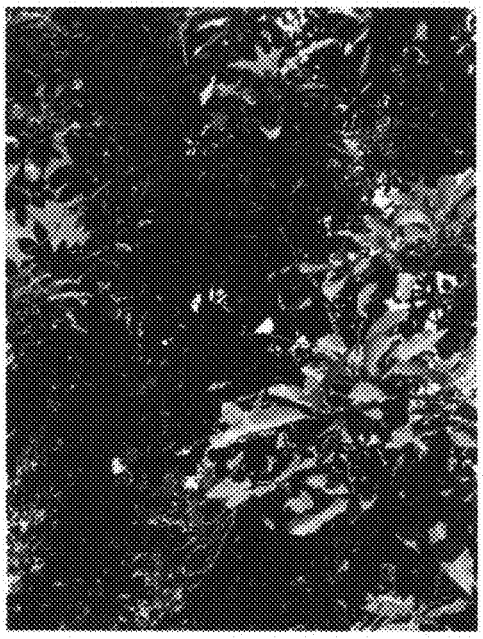
FIG. 3 shows the middle portion of the 'Lali' avocado tree.
Figure 5:
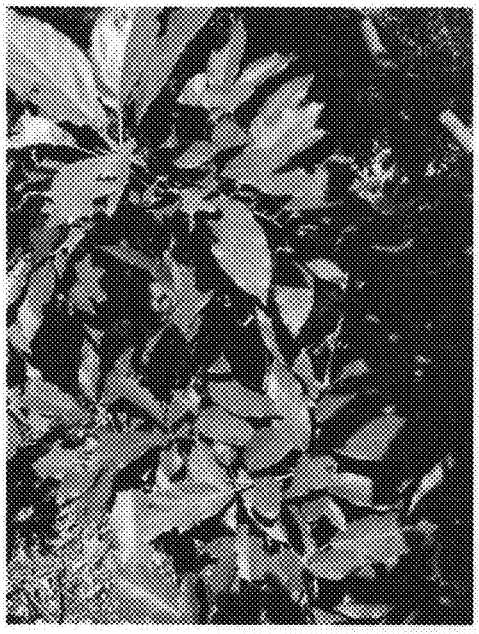
FIG. 5 shows a detailed view of the leaves of the 'Lali' avocado tree.
Figure 8:
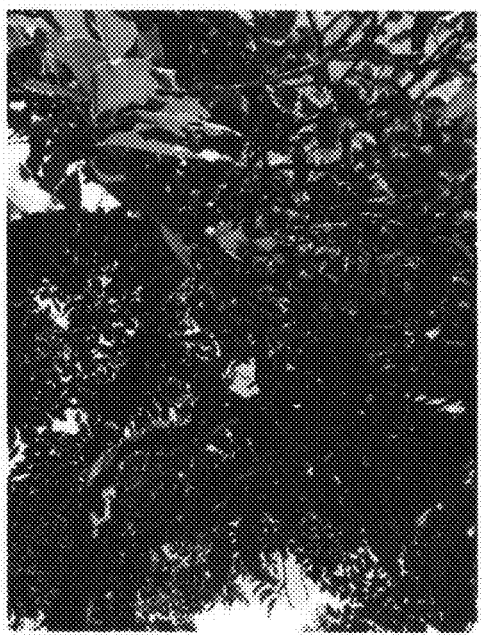
FIG. 8 shows a view of the upper level of the 'Lali' avocado tree.

The leaves are obviate and are light green (HEX value #90EE90) when young, becoming dark green (HEX value #8FBC8F) on their upper surface and a slightly lighter dark seagreen (HEX value #006400) on the underside when mature, and are 3.5" wide by 9" in length as shown in FIG. 5. New leaves have a smooth upper surface marked by a lighter venation that is very slightly raised. Upper and lower leaf surfaces become leathery in texture as they mature, as appears in FIGS. 3, and 5. Veins are prominently raised, and the number of veins from mid-rib average 10. Leaf arrangement and venation pattern is alternating. Vein color is yellow (HEX value #CDCD00). The leaf tip is cuspidate and the base is acute. The margin is entire and undulate. The length of leaf blades varies from 4"-7", and averages about 5.5". Leaf blades have a width of 2" to 3" with an average width of 2.3". The foliage is sparse near the ground, FIGS. 1 and 2, becoming more dense toward the upper regions of the tree, FIGS. 7, 8 and 9. Typical observed petiole lengths are consistent at 1.25", and their diameter is 3.5-3.7 mm. Internodes are between ⅜" and ½". Petiole color is yellow (HEX value #888B00). The leaf angle at the point of attachment is in the range of 45° to 60°.

Buds are yellow-green in color (HEX value #9ACD32), have an average length of 7-11 mm, average width of 3.75-4 mm, and a Lancelot to oblong-Lancelot shape with a rounded base and acute tip. Pedicels are green-yellow in color (HEX value #A2CD5A) and average 6 mm in length and 1.3 mm in width with an average diameter of 1-2 mm.

The flowers of this plant have 3 lobes that are approximately 6.5-6.7 mm in length and 2 mm in width. Margins are smooth and uniform, and the texture is smooth. Densely silk tomentose is found on both surfaces. The shape is apex acute with a flattened base. Inflorescence type is determinate. The flowers are produced in racemes near the ends of the branches, and are furnished with both stamens and pistils, all of them being inherently capable of developing into fruits. Peduncles range from 42 mm to 153 mm and average about 87 mm and are yellow green in color (HEX value #8B7500). Typical observed flower depth is 7.5-8 mm. The flowers are small and pale to yellow green in color (HEX value #8B7500). At first glance they appear to have six lanceolate or ovate petals, but on closer examination these are seen to be perianth-lobes. The usual differentiation into two whorls or series, calyx and corolla, does not occur in this avocado. The perianth-lobes are of nearly equal length with the inner three occasionally being longer than the outer and being more or less pubescent. The nine stamens are arranged in three series. The anthers are 4-celled with the cells opening by small valves hinged at the upper end. At the base of each stamen of the inner series are two large orange-colored glands which secrete nectar, presumably for the attraction of insects. Inside the stamens are three staminodes or vestigial stamens. The ovary is 1-celled, and contains a single ovule. The style is slender, usually hairy, with a simple stigma.

The flowers are not fragrant. The tree blooms in February and the flowers are of the B type which may require an "A" type pollenizer for maximum production.

Figure 10:
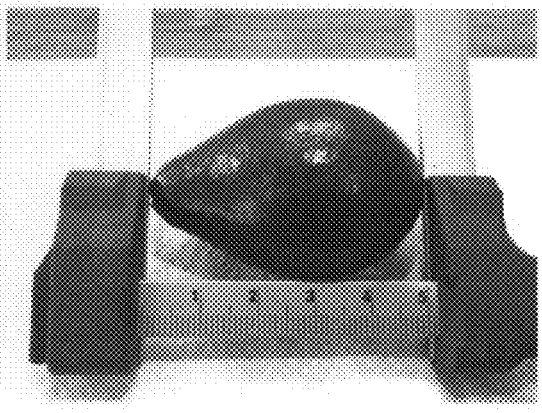
FIG. 10 shows the scale in inches of a typical fruit of the 'Lali' avocado tree measured against a ruler.
Figure 11:
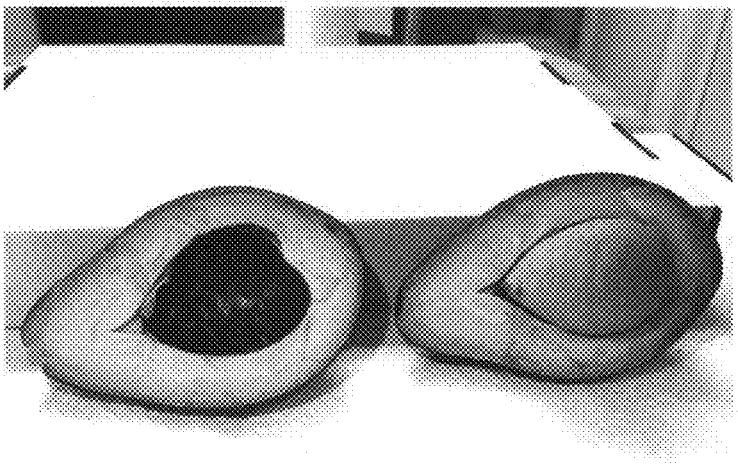
FIG. 11 shows the color and internal configuration of the fruit and the seed of the 'Lali' avocado tree.

As shown in FIG. 10, the fruit shape is an ovate (oval or elongate) berry having a slight taper toward the stem end. The fruit matures in late February and can be picked in late February or March. It averages 3.5" in diameter and 5" in length. The fruit weights are between 14 and 18 ounces. As shown in FIG. 11, the interior of the fruit is seen to have a mesocarp color that is green near the shell and yellow near the seed cavity. The seed is round, weighing about 6.9-7.2 oz, depending on overall fruit size, having a diameter between 2.0 and 2.5". The seed is tight in the cavity, is 2.5" to 3.5" long, and is dark brown in color.

The plant produces fruit at a medium-high volume, averaging about 250-300 lbs per year. The tree exhibits an excellent winter hardiness of 9B. It is not tolerant to flooding, and drought stress has not been observed due to constant irrigation practices. Avocado shelf life is several weeks, and the fruit can be stored above 50° F. The fruit naturally ripens once placed at room temperature or about 5-8 days after harvesting.

This plant differs from other existing cultivars primarily in the lateness of maturity of the fruit, and in the combination of weight, shape, color, and skin texture of the fruit. The fruit is used as a fresh commodity for retail markets.

I claim:

1. A new and distinct variety of avocado tree substantially as described and illustrated and characterized as to novelty by its overall good eating qualities, its medium size and its being ready to be picked in late February and March.

* * * * *